United States Patent [19]

Clémence et al.

[11] Patent Number: 4,636,512
[45] Date of Patent: Jan. 13, 1987

[54] ANTI-INFLAMMATORY 2-SUBSTITUTED-4-HYDROXY-3-QUINOLINE CARBOXAMIDES

[75] Inventors: Francois Clémence; Odile Le Martret, both of Paris; Francoise Delevalleé, Fontenay-sous-Bois, all of France

[73] Assignee: Roussel Uclaf, Paris, France

[21] Appl. No.: 748,743

[22] Filed: Jun. 25, 1985

[30] Foreign Application Priority Data

Jun. 25, 1984 [FR] France .................... 84 09960

[51] Int. Cl.⁴ .................... A61K 31/47; C07D 215/22
[52] U.S. Cl. .................... 514/312; 514/275; 546/156; 544/322
[58] Field of Search .............. 514/312, 275; 546/156; 544/322

[56] References Cited

U.S. PATENT DOCUMENTS

| | | | |
|---|---|---|---|
| 3,992,540 | 11/1976 | Clémence | 546/156 |
| 4,107,310 | 8/1978 | Allais | 546/156 |
| 4,299,831 | 11/1981 | Clémence | 546/156 |
| 4,450,166 | 5/1984 | Clémence | 546/156 |
| 4,523,942 | 6/1985 | Hamprecht | 544/92 |

OTHER PUBLICATIONS

Clémence Chemical Abstracts 100:138971g (12/8/83).

Primary Examiner—Robert J. Warden
Assistant Examiner—Robert Benson
Attorney, Agent, or Firm—Bierman & Muserlian

[57] ABSTRACT

Novel racemates or optically active forms of 2-amino-4-hydroxy-3-quinoline carboxylic acid derivatives of the formula

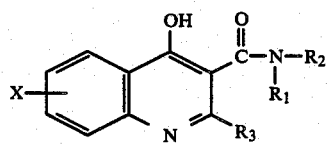

wherein X is in the 5-, 6-, 7- or 8-position and is selected from the group consisting of hydrogen, halogen, alkyl of 1 to 5 carbon atoms, alkoxy of 1 to 4 carbon atoms, $CF_3-$, $CF_3S-$ and $CF_3O-$, $R_1$ is selected from the group consisting of hydrogen and alkyl of 1 to 4 carbon atoms, $R_2$ is selected from the group consisting of (a) thiazolyl, 4,5-dihydrothiazolyl, pyridinyl, oxazolyl, isoxazolyl, imidazolyl, pyrimidyl and tetrazolyl, each optionally substituted with alkyl of 1 to 4 carbon atoms and (b) phenyl optionally substituted with at least one member of the group consisting of hydroxy, alkyl and alkoxy of 1 to 4 carbon atoms, $CF_3-$, $-NO_2$ and halogen, $R_3$ is selected from the group consisting of 2-pyrrolidinyl of the formula

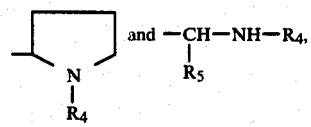

$R_4$ is selected from the group consisting of hydrogen, an amino protective group and

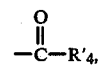

$R'_4$ is selected from the group consisting of alkyl 1 to 5 carbon atoms optionally substituted with amino or protected amino, aryl and aralkyl, $R_5$ is selected from the group consisting of hydrogen, alkyl of 1 to 5 carbon atoms, aryl, aralkyl, p-hydroxy-benzyl, 1H-indol-3-yl methyl of the formula

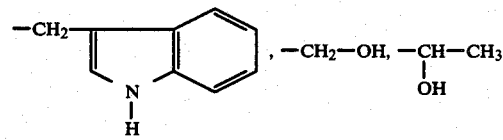

and $-CH_2SH$, the last three being optionally protected by a blocking group and their non-toxic, pharmaceutically acceptable acid addition salts having analgesic and anti-inflammatory activity and novel intermediates.

18 Claims, No Drawings

ANTI-INFLAMMATORY 2-SUBSTITUTED-4-HYDROXY-3-QUINOLINE CARBOXAMIDES

STATE OF THE ART

Related 3-quinoline carboxylic acid derivatives are described in commonly assigned U.S. Pat. Nos. 4,299,831, 4,397,856, 4,107,310 and 4,486,438.

OBJECTS OF THE INVENTION

It is an object of the invention to provide the novel 3-quinoline carboxylic acid derivatives of formula I and their non-toxic, pharmaceutically acceptable acid addition salts and their preparation and novel intermediates therefor.

It is another object of the invention to provide novel analgesic compositions and a novel method of relieving pain in warm-blooded animals.

These and other objects and advantages of the invention will become obvious from the following detailed description.

THE INVENTION

The novel compounds of the invention are selected from the group consisting of racemates or optionally active forms of 2-amino-4-hydroxy-3-quinoline carboxylic acid derivatives of the formula

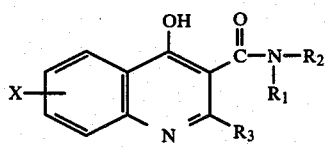

wherein X is in the 5-, 6-, 7- or 8-position and is selected from the group consisting of hydrogen, halogen, alkyl of 1 to 5 carbon atoms, alkoxy of 1 to 4 carbon atoms, $CF_3—$, $CF_3S—$ and $CF_3O—$, $R_1$ is selected from the group consisting of hydrogen and alkyl of 1 to 4 carbon atoms, $R_2$ is selected from the group consisting of (a) thiazolyl, 4,5-dihydrothiazolyl, pyridinyl, oxazolyl, isoxazolyl, imidazolyl, pyrimidyl and tetrazolyl, each optionally substituted with alkyl of 1 to 4 carbon atoms and (b) phenyl optionally substituted with at least one member of the group consisting of hydroxy, alkyl and alkoxy of 1 to 4 carbon atoms, $CF_3—$, $—NO_2$ and halogen, $R_3$ is selected from the group consisting of 2-pyrrolidinyl of the formula

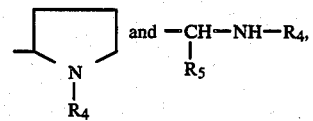

$R_4$ is selected from the group consisting of hydrogen, an amino protective group and

$R'_4$ is selected from the group consisting of alkyl 1 to 5 carbon atoms optionally substituted with amino or protected amino, aryl and aralkyl, $R_5$ is selected from the group consisting of hydrogen, alkyl of 1 to 5 carbon atoms, aryl, aralkyl, p-hydroxy-benzyl, 1H-indol-3-yl methyl of the formula

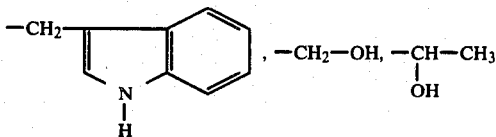

and $—CH_2SH$, the last three being optionally protected by a blocking group and their non-toxic, pharmaceutically acceptable acid addition salts.

Since the compounds of formula I possess at least one asymmetric carbon atom, they exist in the form of racemates or as optically active isomers.

Examples of X are hydrogen, halogens such as bromine, iodine and preferably chlorine; alkyl such as methyl, ethyl, n-propyl, isopropyl, n-butyl, isobutyl and n-pentyl; alkoxy such as methoxy, ethoxy and n-propoxy; and $CF_3—$, $CF_3S—$ and $CF_3O—$. Examples of $R_1$ are hydrogen and alkyl such as methyl and ethyl.

When $R_2$ is one of the recited heterocycles substituted by alkyl, the alkyl is preferably methyl or ethyl. When $R_2$ is phenyl substituted with at least one group, the substituent is preferably —OH, methyl, ethyl, methoxy, ethoxy, $—NO_2$, $CF_3—$ or chlorine.

When $R_4$ is

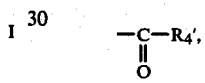

$R_4'$ is preferably alkyl, for example methyl, ethyl, n-propyl, isopropyl, n-butyl, isobutyl or n-pentyl. When $R_4'$ is aryl or aralkyl, it is preferably phenyl or benzyl, respectively.

A protective group of the amino function is understood to be a group which can easily be eliminated, for example by hydrolysis or reduction. Radicals capable of effectively protecting an amino are generally acids, for example an acyl derived from an aliphatic, aromatic, araliphatic or heterocyclic carboxylic acid such as acetic acid, benzoic acid or pyridine-carboxylic acid or an acyl derived from a carbonic acid such as ethoxy-carbonyl, benzyloxy-carbonyl (=Z), tert-butyloxy-carbonyl (=Boc) or p-methyloxybenzyloxy-carbonyl, or an acyl derived from a sulfonic acid such as benzenesulfonyl or p-toluenesulfonyl, but there can also be utilized other groups such as aryl or aralkyl optionally substituted for example benzyl and triphenylmethyl or 0-nitrophenyl-sulfenyl and 2-benzoyl-1-methylvinyl.

When $R_5$ is alkyl, aryl or aralkyl, it is preferably one of the radicals previously mentioned for $R_4'$.

The protective groups for the thiol function are, for example, benzyl, benzyloxycarbonyl or tert-butyloxycarbonyl. The protective groups for the alcohol function are, for example, benzyl, tert-butyl or benzyloxycarbonyl.

Examples of suitable acids for the formation, of the non-toxic, pharmaceutically acceptable acid addition salts are mineral acids such as hydrochloric acid, hydrobromic acid, sulfuric acid and phosphoric acid, as well as sulfonic acids such as alkyl or arylsulfonic acids, for example, methanesulfonic or p-toluenesulfonic acid.

Among the preferred compounds of the invention are those of formula I wherein X is in the 8-position and is preferably $CF_3—$, those wherein $R_1$ is hydrogen, those wherein R₂ is thiazolyl and those wherein R₄ is hydrogen in their racemic or optically active form and their non-toxic, pharmaceutically acceptable acid addition salts and especially those in their (S) optically active form and their acid addition salts.

The preferred amino protective groups have the formula —COOA wherein A is alkyl of 1 to 5 carbon atoms, aryl or aralkyl in their racemic or optically active forms and their acid addition salts. Particularly preferred are those groups wherein A is tert.butyl or benzyl in their racemic or optically active form and their acid addition salts.

The novel process of the invention for the preparation of compounds of formula I comprises reacting a compound of the formula

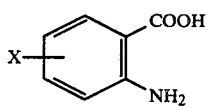  II wherein X has the above definition with a racemic or optically active form of an amino acid of the formula

R₃—COOH            III in activated form wherein R₃ is

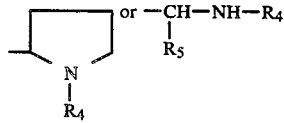

and R₄ is an amino protective group or

wherein R₄' has the above definition and R₅ had the above definition with a proviso that when R₅ is —CH₂OH,

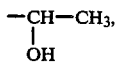

or —CH₂SH and when R₄' is alkyl substituted with amino, the active functions are possibly blocked to obtain a compound in racemic or optically form of the formula

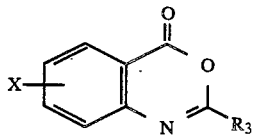  IV wherein X and R₃ have the above definition, reacting the latter in the presence of a base with a compound of the formula

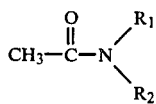  V to obtain a compound in racemic or optically active form of the formula

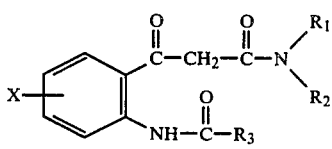  VI wherein X, R₁, R₂ and R₃ have the above definition and cyclizing the latter in the presence of an alkaline agent to obtain the corresponding compound of formula I in racemic or optically active form and optionally subjecting the latter to the action of one or more agents to remove the protective groups to obtain a compound of formula I wherein R₃ is

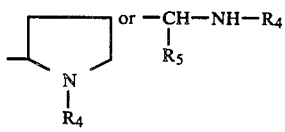

and R₄ is hydrogen or

and R₅ and R₄' are defined above without protective groups in racemic or optically active form and the latter is optionally reacted with an acid to obtain the corresponding non-toxic, pharmaceutically acceptable acid addition salt.

Preferably, the activation of the amino acid of formula III is an non-racemizing process and the amino acid is most preferably activated in the form of a mixed anhydride with isobutyl chloroformate although other alkyl chloroformates may be used. Other activation methods known from peptide synthesis such as using dicyclohexylcarbodiimide activated by hydroxybenzotriazole may be used. The reaction of the compounds of formulae II and III may be effected at −20° to 0° C. in the presence of a base such as N-methyl-morpholine, N-ethyl-morpholine or triethylamine.

The reaction of the compounds of formulae IV and V is effected in the presence of a base such as an organolithium like n-butyllithium or a lithium amide like lithium diisopropylamide at low temperatures of about −70° C. The cyclization of the compound of formula VI is effected in the presence of an alkaline agent such as an alkali metal hydride like sodium hydride, an alkali metal carbonate like sodium carbonate or potassium carbonate or an amine such as piperidine, 4-amino-pyridine, 4-dimethylamino-pyridine, triethylamine, 1,5-diazabicyclo-[4,3,0]-non-5-ene, 1,4-diazabicyclo-[2,2,2]-octane or 1,5-diazabicyclo-[5,4,0]-undec-5-ene.

The deblocking agents for the removal of the protective groups will depend on the particular protective group used. When the protective group is Boc, the deblocking may be effected by acid hydrolysis such as in the presence of trifluoroacetic acid or hydrochloric acid or by the action of boron tribromide. If the protective group is Z or benzyl, the deblocking can be effected by catalytic hydrogenation.

In a variation of the process of the invention for the preparation of compounds of formula I wherein R₃ is

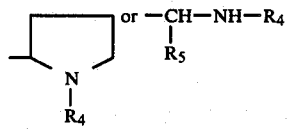

and R₄ is

and R₄' is alkyl of 1 to 5 carbon atoms optionally containing a free or protected amino group or aryl or aralkyl, a compound of formula I wherein R₃ is 2-pyrrolidinyl or

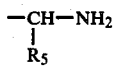

in racemic or optically active form is reacted with a reactive derivative of

to obtain the corresponding compound of formula I in racemic or optically active form and optionally subjecting the latter to a deblocking agent to remove the amino protective group and optionally salifying the latter with an acid to form the acid addition salt thereof.

In this latter process, the reactive derivative of

is an acid anhydride or acid halide and the reaction is effected in the presence of a base such as pyridine or N-methylmorpholine. The deblocking agent is selected as above.

The starting materials of formula II are known and may be prepared by known processes such as those described in French Pat. No. 2.157.874.

The novel analgesic and anti-inflammatory compositions of the invention are comprised of an analgesically and anti-inflammatorily effective amount of at least one compound of formula I and their non-toxic, pharmaceutically acceptable acid addition salts and an inert pharmaceutical carrier. The compositions may be in the form of tablets, dragees, capsules, granules, suppositories, ointments, creams, gels, injectable solutions or suspensions and aerosols.

Examples of suitable excipients or inert pharmaceutical carriers are talc, gum arabic, lactose, starch, magnesium stearate, cocoa butter, aqueous and non-aqueous vehicles, animal or vegetable fatty substances, paraffinic derivatives, glycols, various wetting dispersing or emulsifying agents and preservatives.

The compositions are useful for the treatment of degenerative inflammatory maladies such as osteroarthrosis, various collagen diseases such as tendinitis, rheumatic maladies such as rheumatoid polyarthritis and ankylosing spondylarthritis and the treatment of maladies of an auto-immune nature such as disseminated erythematous lupus, glomerulonephritis, multiple sclerosis, etc. They are also useful for the treatment of muscular, articular or nervous alginas, tooth pain, migraines, shingles and as a complementary treatment of infections and febrile states.

Especially preferred are those compositions wherein R₄ in the compound of formula I is hydrogen in racemic or optically active form and their acid addition salts and those compounds of formula I in their optically active (S) form and their acid addition salts.

The novel method of the invention for relieving pain and inflammation in warm-blooded animals, including humans, comprises administering to warm-blood animals an analgesically and anti-inflammatorily effective amount of at least one compound of formula I and their non-toxic, pharmaceutically acceptable acid addition salts. The compounds may be administered orally, rectally, parenterally or topically to the skin and mucosa. The usual daily dose is 0.25 to 25 mg/kg depending on the conditions treated, the specific compound and the method of administration.

The novel intermediates of the invention are the compounds of formulae IV and VI with the exception of the compounds of formula IV

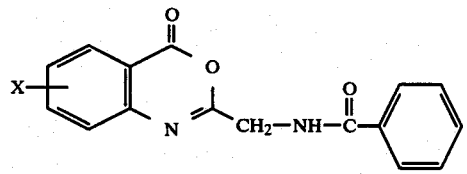

wherein X is hydrogen, chlorine, bromine or iodine.

In the following examples, there are described several preferred embodiments to illustrate the invention. However, it is to be understood that the invention is not intended to be limited to the specific embodiments.

EXAMPLE 1

1,1-dimethylethyl N-[[4-hydroxy-8-(trifluoromethyl)-3-[(2-thiazolylamino)-carbonyl]-quinolin-2-yl]-methyl]-carbamate

STEP A: 1,1-dimethylethyl [(4-oxo-8-(trifluoromethyl)-4H-3,1-benzoxazin-2-yl)-methyl]-carbamate A mixture of 17.5 g of N-BOC glycine, 100 ml of methylene chloride and 13.7 ml of N-methyl-morpholine was cooled to −20° C. and a solution of 13 ml of isobutyl chloroformate in 50 ml of methylene chloride was added. After stirring for 30 minutes at −20° C., a solution of 10.25 g of 2-amino-3-trifluoromethyl benzoic acid [prepared by the process of J. Med. Chem., Vol. 16 (2) 101,6 (1973)] in 5.49 ml of N-methyl-morpholine and 120 ml of methylene chloride was added thereto and after stirring for 20 hours at ambient temperature, the mixture was poured into 500 ml of water and 150 ml of 2N hydrochloric acid. The mixture was extracted with methylene chloride and the organic phase was washed with water, dried and concentrated under reduced pressure to dryness. The residue was triturated with 50 ml of methanol and the mixture was frozen, separated, washed with methanol and dried under reduced pressure at 50° C. to obtain 11 g of 1,1-dimethylethyl [(4-oxo-8-(trifluoromethyl)-4H-3,1-benzoxazin-2-yl)-methyl]-carbamate melting at 176° C.

Analysis: Calculated: %C, 52.33; %H, 4.39; %N, 8.14; %F, 16.55. Found: %C, 52.5; %H, 4.4; %N, 7.9; %F, 16.7.

STEP B: 1,1-dimethylethyl N-[2-[[2-[1,3-dioxo-3-(2-thiazolylamino)-propyl]-6-trifluoromethylphenyl]-amino]-2-oxo-ethyl]-carbamate A solution of 85.6 ml of n-butyllithium in hexane was introduced into 8.5 g of N-2-thiazolyl acetamide suspended in 260 ml of tetrahydrofuran. After cooling to −75° C., a solution of 10.33 g of the product of Step A in 75 ml of tetrahydrofuran was added at this temperature. The reaction mixture was poured into 400 ml of water and 100 ml of 2N hydrochloric acid, and was extracted with ether. The organic phase was washed with N hydrochloric acid, then with water, dried, and concentrated to dryness under reduced pressure. The orange oil residue crystallized and the residue was triturated in ether, separated, washed with ether, and dried under reduced pressure to obtain 7.7 g of 1,1-dimethylethyl N-[2-[[2-[1,3-dioxo-3-(2-thiazolylamino)-propyl]-6-trifluoromethylphenyl]-amino]-2-oxo-ethyl]-carbamate melting at 166° C.

Analysis: Calculated: %C, 49.38; %H, 4.36; %N, 11.52; %F, 11.72; %S, 6.59. Found: %C, 49.2; %H, 4.3; %N, 11.3; %F, 11.7; %S, 6.5.

STEP C: 1,1-dimethylethyl N-[[4-hydroxy-8-(trifluoromethyl)-3-[(2-thiazolylamino)-carbonyl]-quinolin-2-yl]-methyl]-carbamate 7.3 g of the product of Step B, 140 ml of tetrahydrofuran and 2.4 g of 4-dimethylamino-pyridine were stirred for 1 hour at ambient temperature and the solvent was eliminated under reduced pressure. The residue was taken up in 100 ml of water and 20 ml of N hydrochloric acid and the solution was extracted with a mixture of ethyl acetate and tetrahydrofuran. After washing the organic phase with water and drying and concentrating the filtrate under reduced pressure, 7 g of crude product were obtained which was triturated in ether, separated, washed with ether and dried under reduced pressure at 60° C. to obtain 6.6 g of 1,1-dimethylethyl N-[[4-hydroxy-8-(trifluoromethyl)-3-[(2-thiazolylamino)-carbonyl]quinolin-2-yl]-methyl]-carbamate melting at 238° C.

Analysis: Calculated: %C, 51.28; %H, 4.09; %N, 11.96; %F, 12.17; %S, 6.84. Found: %C, 51.1; %H, 4.0; %N, 11.8; %F, 11.9; %S, 6.9.

EXAMPLE 2

2-(aminomethyl)-4-hydroxy-N-(2-thiazolyl)-8-trifluoromethyl-3-quinoline carboxamide 6.2 g of the product of Example 1, 125 ml of methylene chloride and 63 ml of trifluoroacetic acid were stirred for 1 hour at ambient temperature and the solvents were eliminated under reduced pressure. The residue was taken up in 100 ml of water and the pH was brought to 7 by addition of saturated aqueous solution of sodium bicarbonate. After separating, washing with water and drying under reduced pressure at 100° C., 4.8 g of 2-(aminomethyl)-4-hydroxy-4-N-(2-thiazolyl)-8-trifluoromethyl-3-quinoline-carboxamide melting at about 280° C. were obtained.

Analysis: Calculated: %C, 48.91; %H, 3.01; %N, 15.21; %F, 15.47; %S, 8.70. Found: %C, 49.0; %H, 3.2; %N, 15.3; %F, 15.1; %S, 8.6.

EXAMPLE 3

1,1-dimethylethyl N-[(R) 1-[4-hydroxy-3-[(2-thiazolylamino)-carbonyl]-8-(trifluoromethyl)-quinolin-2-yl]-ethyl]-carbamate STEP A: 1,1-dimethylethyl N-[(R) 1-[4-oxo-8-(trifluoromethyl)-4H,3,1-benzoxazin-2-yl]-ethyl]-carbamate 18.9 g of BOC-D-alanine, 25 ml of N-methyl-morpholine and 200 ml of methylene chloride were mixed together, cooled to −20° C. and 26 ml of isobutyl chloroformate in solution in 100 ml of methylene chloride were added. The suspension obtained was maintained at −20° C. and a solution of 20.5 g of 2-amino-3-trifluoromethylbenzoic acid in 10 ml of morpholine and 200 ml of methylene chloride was added. The temperature was allowed to return to room temperature and the mixture was stirred for 2 hours and then was poured into 400 ml of hydrochloric acid. The organic phase was washed with 250 ml of a 10% aqueous solution of sodium carbonate, then with water, dried and concentrated to dryness under reduced pressure to obtain 17.6 g of 1,1-dimethylethyl N-[(R) 1-[4-oxo-8-(trifluoromethyl)-4H,3,1-benzoxazin-2-yl]-ethyl]-carbamate melting at 175° C. and having a specific rotation of $[\alpha]_D = +68° \pm 2°$ (c=0.8% in $CH_3COOH$).

STEP B: 1,1-dimethylethyl N-[(R) 2-[[2-[1,3-dioxo-3-(2-thiazolyl)-amino)-propyl]-6-(trifluoromethyl)-phenyl]-amino]-1-methyl-2-oxoethyl]-carbamate 128.6 ml of a solution of n-butyllithium was added with stirring under nitrogen to a solution of 12.78 g of N-(2-thiazolyl)-acetamide in 370 ml of tetrahydrofuran at −3° to 1° C. After 15 minutes, this solution was cooled to −70° C. and at this temperature, 10.75 g of the product of Step A in 75 ml of tetrahydrofuran were added. After 30 minutes at −70° C., this was poured into 140 ml of N hydrochloric acid and the mixture was extracted with ethyl acetate. The organic phase was dried and concentrated to dryness under reduced pressure. The residue was taken up in 350 ml of ether and 250 ml of N hydrochloric acid and the mixture was concentrated to dryness under reduced pressure to obtain 14.1 g of 1,1-dimethylethyl N-[(R)2-[[2-[1,3-dioxo-3-(2-thiazolyl)-amino)-propyl]-6-(trifluoromethyl)-phenyl]-amino]-1-methyl-2-oxo-ethyl]-carbamate.

STEP C: 1,1-dimethylethyl N-[(R) 1-[4-hydroxy-3-[(2-thiazolyl)-amino)-carbonyl]-8-(trifluoromethyl)-quinolin-2-yl]-ethyl]-carbamate A mixture of 13.8 g of the product of Step B, 3.8 g of dimethylaminopyridine, and 120 ml of tetrahydrofuran was left in contact for 2 days at ambient temperature and then the tetrahydrofuran was expelled. The residue was taken up in 40 ml of N hydrochloric acid and the mixture was stirred for 10 minutes, filtered and washed with water. The crude product was purified by treatment at reflux, without total solution, in 500 ml of methanol and after cooling 9.4 g of 1,1-dimethylethyl N-[(R) 1-[4-hydroxy-3-[(2-thiazolylamino)-carbonyl]-8-(trifluoromethyl)-quinolin-2-yl]-ethyl]-carbamate were obtained melting at 265° C. and having a specific rotation $[\alpha]_D = -66.5°$ C.±1.5° (c=1% in acetic acid).

Analysis: Calculated: %C, 52.27; %H, 4.39; %N, 11.61; %F, 11.81; %S, 6.64. Found: %C, 52.4; %H, 4.4; %N, 11.5; %F, 11.7; %S, 6.8.

EXAMPLE 4

2-[(R) 1-aminoethyl]-4-hydroxy-N-(2-thiazolyl)-8-trifluoromethyl-3-quinoline carboxamide 7 g of the product of Example 3 were suspended in 140 ml of methylene chloride and 70 ml of trifluoroacetic acid were slowly added with the temperature falling to 15° C. Contact was maintained for 4 hours and then, after concentrating to dryness under reduced pressure, the residue was taken up in 100 ml of ether. The crystals were separated by filtration and the product was slowly added to 50 ml of a 10% aqueous solution of sodium bicarbonate. After stirring, filtration, and washing with water, the crude product was treated at reflux with 300 ml of methanol without complete solution and after cooling and concentrating to 50 ml, 2.3 g of 2-[(R) 1-aminoethyl]-4-hydroxy-N-(2-thiazolyl)-8-trifluoromethyl-3-quinoline-carboxamide melting at 265° C. and with a specific rotation of $[\alpha]_D = -72°±2.5°$ (c=0.5% in CH$_3$COOH) were obtained.

Analysis: Calculated: %C, 50.26; %H, 3.43; %F, 14.90; %S, 8.39; %N, 14.73. Found: %C, 50.3; %H, 3.6; %F, 15.0; %S, 8.4; %N, 14.5.

EXAMPLE 5

1,1-dimethylethyl N-[(S) 1-[4-hydroxy-3-[(2-thiazolylamino)-carbonyl]-8-trifluoromethyl-quinolin-2-yl]-ethyl]-carbamate STEP A: 1,1-dimethylethyl N-[(S) 1-[4-oxo-8-(trifluoromethyl)-4H-3,1-benzoxazin-2-yl]-ethyl]-carbamate Using the procedure used for the antipode (R) prepared in Step A of Example 3, BOC-L-alanine was reacted to obtain 21.4 g of 1,1-dimethylethyl N-[(S) 1-[4-oxo-8-(trifluoromethyl)-4H-3,1-benzoxazin-2-yl]-ethyl]-carbamate melting at 174° C. and having a specific rotation of $[\alpha]_D = -66.5°±1.5°$ (c=1% in CH$_3$COOH)

Analysis: Calculated: %C, 53.63; %H, 4.78; %N, 7.82; %F, 15.90. Found: %C, 54.1; %H, 5.00; %N, 7.6; %F, 15.6.

STEP B: 1,1-dimethylethyl N-[(S) 2-[[2-[1,3-dioxo-3-(2-thiazolylamino)-propyl]-6-(trifluoromethyl)-phenyl]-amino]-1-methyl-2-oxoethyl]-carbamate Using the procedure of Step B of Example 3, 14.1 g of 1,1-dimethylethyl N-[(S) 2-[[2-[1,3-dioxo-3-(2-thiazolylamino)-propyl]-6-(trifluoromethyl)-phenyl]-amino]-1-methyl-2-oxo-ethyl]-carbamate were obtained.

STEP C: 1,1-dimethylethyl N [(S) 1-[4-hydroxy-3-[2-thiazolylamino]-carbonyl]-8-(trifluoromethyl)-quinolin-2-yl]-ethyl]-carbamate Using the procedure of Step C of Example 3, 13.4 g of the product of Step B, 3.7 g of 4-dimethyl-amino-pyridine and 120 ml of tetrahydrofuran were reacted and the product obtained was purified by treatment at reflux in 700 ml of methanol to obtain 6.6 g of 1,1-dimethylethyl N-[(S) 1-[4-hydroxy-3-[2-thiazolylamino)-carbonyl]-8-(trifluoromethyl)-quinolin-2-yl]-ethyl]-carbamate melting at 265° C. and having a specific rotation of $[\alpha]_D = +61°±2.5°$ (c=0.5% in acetic acid).

Analysis: Calculated: %C, 52.27; %H, 4.39; %N, 11.61; %F, 11.81; %S, 6.64. Found: %C, 52.4; %H, 4.4; %N, 11.4; %F, 11.7; %S, 6.9.

EXAMPLE 6

2-[(S) 1-aminomethyl]-4-hydroxy-N-(2-thiazolyl)-8-trifluoromethyl-3-quinoline carboxamide Using the procedure of Example 4, 4.95 g of the product of Example 5 were reacted to obtain 4.1 g of crude product. The crude product was purified by treatment at reflux in 360 ml of methanol and the crystals obtained were filtered hot to obtain 1.5 g of 2-[(S) 1-aminoethyl]-4-hydroxy-N-(2-thiazolyl)-8-trifluoromethyl-3-quinoline carboxamide melting at 270° C. and having a specific rotation of $[\alpha]_D = +62°±3°$ (c=0.3% in acetic acid).

Analysis: Calculated: %C, 50.26; %H, 3.63; %F, 14.90; %S, 8.39; %N, 14.73. Found: %C, 50.1; %H, 3.4; %F, 15; %S, 8.5; %N, 14.4.

EXAMPLE 7

1,1-dimethylethyl N-[(S) 1-[4-hydroxy-3-[(2-thiazolyl-amino)-carbonyl]-8-(trifluoromethyl)-quinolin-2-yl]-propyl]-carbamate STEP A: 1,1-dimethylethyl N-[(S) 1-[4-oxo-8-(trifluoromethyl)-4H-3,1-benzoxazin-2-yl]-propyl]-carbamate A solution of 10.16 g of BOC-L-amino butyric acid in 100 ml of methylene chloride and 13.7 ml of N-methyl-morpholine was cooled to −20° C. and at this temperature, 13 ml of isobutyl chloroformate and 50 ml of methylene chloride were introduced with stirring for 30 minutes at −20° C. to −15° C. At −20° C., a solution of 10.25 g of 2-amino-3-trifluoromethyl-benzoic acid in 100 ml of methylene chloride and 5.49 ml of N-methyl-morpholine was added. After stirring the mixture for 20 hours at ambient temperature, the mixture was poured into 200 ml of N hydrochloric acid and was extracted with methylene chloride. The organic phase was washed with water, then with sodium bicarbonate, washed again with water and dried. The filtrate was concentrated to dryness under reduced pressure and the residue obtained was triturated in isopropanol, separated, washed with isopropanol and dried under reduced pressure at 70° C. to obtain 9.9 g of 1,1-dimethylethyl N-[(S) 1-[4-oxo-8-(trifluoromethyl)-4H-3,1-benzoxazin-2-yl]-propyl]-carbamate melting at 136°–138° C. and having a specific rotation of $[\alpha]_D = -68°±1.5°$ (c=1% in CH$_3$COOH).

Analysis: Calculated: %C, 54.84; %H, 5.14; %N, 7.52; %F, 15.31. Found: %C, 54.9; %H, 5.2; %N, 7.2; %F, 15.4.

STEP B: 1,1-dimethylethyl N-[(S) 2-[[2-[1,3-dioxo-3-(2-thiazolylamino)-propyl]-6-(trifluoromethyl)-phenyl]-amino]-1-ethyl-2-oxoethyl]-carbamate Using the procedure of Step B of Example 3, 7.78 g of N-(2-thiazolyl)-acetamide, 240 ml of tetrahydrofuran and 78.3 ml of a solution of n-butyllithium in hexane and 10.2 g of the product of Step A in 75 ml of tetrahydrofuran were reacted to obtain 8.3 g of 1,1-dimethylethyl N-[(S) 2-[[2-[1,3-dioxo-3-(1,1-dimethylethyl N-[(S) 2-[[2-[1,3-dioxo-3-(2-thiazolylamino)-propyl]-6-(trifluoromethyl)-phenyl]-amino]-1-ethyl-2-oxoethyl]-carbamate melting at 190° C. and having a specific rotation of [α]$_D$=−36.5°±2° (c=0.5% in CH$_3$COOH).

STEP C: 1,1-dimethylethyl N-[(S) 1-[4-hydroxy-3-[(2-thiazolylamino)-carbonyl]-8-(trifluoromethyl)-quinolin-2-yl]-propyl]carbamate Using the procedure of Step C of Example 3, 8 g of the product of Step B, 80 ml of tetrahydrofuran and 1.9 g of 4-dimethylaminopyridine were reacted to obtain 6.8 g of 1,1-dimethylethyl N-[(S) 1-[4-hydroxy-3-[(2-thiazolyl-amino)-carbonyl]-8-(trifluoromethyl)-quinolin-2-yl]-propyl]-carbamate melting at 260°–262° C. and having a specific rotation of [α]$_D$=+66.5°±2.5° (c=0.7% in CH$_3$COOH).

Analysis: Calculated: %C, 53.22; %H, 4.67; %N, 11.28; %F, 11.48; %S, 6.46. Found: %C, 52.9; %H, 4.8; %N, 11.1; %F, 11.5; %S, 6.4.

EXAMPLE 8

2-[(S) 1-aminopropyl]-4-hydroxy-N-(2-thiazolyl)-8-trifluoromethyl-3-quinoline carboxamide A mixture of 6.5 g of the product of Example 7, 130 ml of methylene chloride and 65 ml of trifluoroacetic acid was stirred for 2 hours at ambient temperature and then the methylene chloride and trifluoroacetic acid were eliminated under reduced pressure. The residue was taken up in iced water and the pH was adjusted to 7 with a solution of sodium bicarbonate. The mixture was filtered and the product was washed and dried under reduced pressure at 100° C. The product obtained was dissolved at reflux in 120 ml of acetonitrile and the solution was filtered. The filtrate was concentrated to 100 ml and the crystals obtained were frozen, separated, washed and dried under reduced pressure at 100° C. to obtain 3.25 g of 2-[(S) 1-aminopropyl]-4-hydroxy-N-(2-thiazolyl)-8-trifluoromethyl-3-quinoline-carboxamide melting at 206° C. and having a specific rotation of [α]$_D$=+177°±2.5° (c=0.8% in CH$_3$COOH).

Analysis: Calculated: %C, 5.51; %H, 3.81; %N, 14.13; %F, 14.38; %S, 8.09. Found: %C, 51.5; %H, 3.8; %N, 14.0; %F, 14.5; %S, 8.0.

EXAMPLE 9

1,1-dimethylethyl N-[(S)-1-[4-hydroxy-3-[(2-thiazolylamino)-carcarbonyl]-8-(trifluoromethyl)-quinolin-2-yl]-2-methylpropyl]-carbamate STEP A: 1,1-dimethylethyl N-[(S)(2-methyl-1-(4-oxo-8-trifluoromethyl)-4H-3,1-benzoxazin-2-yl)-propyl]-carbamate Using the procedure of Step A of Example 7, a solution of 17.4 g of BOC-L-Valine in 200 ml of methylene chloride, 20.2 ml of N-methyl-morpholine, 20.8 ml of isobutyl chloroformate in 100 ml of methylene chloride, and a solution of 16.4 g of 2-amino-3-trifluoromethyl benzoic acid in 200 ml of methylene chloride and 8.8 ml of N-methyl-morpholine were reacted to obtain 12 g of 1,1-dimethylethyll N-[(S)(2-methyl-1-(4-oxo-8-trifluoromethyl)-4H-3,1-benzoxazin-2-yl)-propyl]carbamate melting at 165° C. and having a specific rotation of [α]$_D$=−61°±2.5° (c=0.6% in CH$_3$COOH).

STEP B: 1,1-dimethylethyl N-[(S) 1-[[2-[1,3-dioxo-3-(2-thiazolylamino)-propyl]-6-(trifluoromethyl)-phenyl]-aminocarbonyl]-2-methylpropyl]-carbamate Using the procedure of Step B of Example 7, a solution of 13.25 g of 2-acetylaminothiazole in 400 ml of tetrahydrofuran, 133 ml of n-butyllithium and a solution of 12 g of product of Step A in 85 ml of tetrahydrofuran were reacted to obtain 15.2 g of 1,1-dimethylethyl N-[(S) 1-[[2-[1,3-dioxo-3-(2-thiazolylamino)-propyl]-6-(trifluoromethyl)-phenyl]-aminocarbonyl]-2-methylpropyl]-carbamate melting at 120° C. and having a specific rotation of [α]$_D$=−49.5°±2° (c=0.9% in CH$_3$COOH).

STEP C: 1,1-dimethylethyl N-[(S)-1-[4-hydroxy-3-[(2-thiazolylamino)-carbonyl]-8-(trifluoromethyl)-quinolin-2-yl]-2-methylpropyl]-carbamate Using the procedure of Step C of Example 7, 15.2 g of the product of Step B in 150 ml of tetrahydrofuran and 4 g of 4-dimethylaminopyridine were reacted to obtain 9.35 g of 1,1-dimethylethyl N-[(S) 1-[4-hydroxy-3-[2-thiazolylamino)-carbonyl]-8-(trifluoromethyl)-quinolin-2-yl]-2-methylpropyl]-carbamate melting at 222° C. and having a specific rotation of [α]$_D$=+50.5°±1° (c=1% in CH$_3$COOH).

Analysis: Calculated: %C, 54.11; %H, 4.94; %F, 11.16; %N, 10.97; %S, 6.28. Found: %C, 53.80; %H, 5.00; %F, 11.00; %N, 10.80; %S, 6.40.

EXAMPLE 10

Trifluoroacetate of 2-[(S) 1-amino-2-methylpropyl]-4-hydroxy-N-(2-thiazolyl)-8-(trifluoromethyl)-3-quinoline carboxamide Using the procedure of Example 8, 10.18 g of the product of Example 9 in 100 ml of methylene chloride and 50 ml of trifuloroacetic acid were reacted to obtain 10.2 g of trifluoroacetate of 2-[(S) 1-amino-2-methylpropyl]-4-hydroxy-N-(2-thiazolyl)-8-(trilfuoromethyl)-3-quinoline carboxamide melting at 164° C. and having a specific rotation of [α]$_D$=−26.5°±1° (c=1.2% in CH$_3$COOH).

Analysis: Calculated: %C, 45.80; %H, 3.45; %F, 21.73; %N, 10.68; %S, 6.11. Found: %C, 45.60; %H, 3.50; %F, 21.80; %N, 10.70; %S, 6.10.

EXAMPLE 11

1,1-dimethylethyl N-[(S) 1-[4-hydroxy-3-[(2-thiazolylamino)-carbonyl]-8-(trifluoromethyl)-quinolin-2-yl]-2-(1H-indol-3-yl)-ethyl]-carbamate STEP A: 1,1-dimethylethyl N-[(S) 2-[1H-indol-3-yl]-1-[4-oxo-8-trifluoromethyl-4H-3,1-benzoxazin-2-yl]-ethyl]-carbamate Using the procedure of Step A of Example 7, a solution of 22.8 g of BOC-L-Tryptophane in 150 ml of methylene chloride and 20.6 g of N-methyl-morpholine, 19.5 ml of isobutyl chloroformate in 75 ml of methylene chloride, 15.4 g of 2-amino-3-trifluoromethyl benzoic acid in 150 ml of methylene chloride and 8.3 ml of N-methyl-morpholine were reacted to obtain 20.7 g of 1,1-dimethylethyl N-[(S) 2-[1H-indol-3-yl]-1-[4-oxo-8-trifluoromethyl-4H-3,1-benzoxazin-2-yl]-ethyl-carbamate melting at 166° C. and having a specific rotation of [α]$_D$= −52°±2.5° (c=0.4% in CH$_3$COOH).

Analysis: Calculated: %C, 60.88; %H, 4.68; %N, 8.87; %F, 12.04. Found: %C, 61.2; %H, 4.8; %N, 8.8; %F, 11.9.

STEP B: 1,1-dimethylethyl N-[(S) 1-[[2-[1,3-dioxo-3-(2-thiazolylamino)-propyl]-6-(trifluoromethyl)-phenyl]-aminocarbonyl]-2-(1H-indol-3-yl)-ethyl]-carbamate Using the procedure of Step B of Example 7, a solution of 18.34 g of 2-acetylaminothiazole in 565 ml of tetrahydrofuran, 184 ml of a solution of n-butyllithium in hexane and 20.3 g of the product of Step A in 150 ml of tetrahydrofuran were reacted to obtain 28 g of 1,1-dimethylethyl N-[(S) 1-[[2-[1,3-dioxo-3-(2-thiazolylamino)-propyl]-6-(trifluoromethyl)-phenyl]-aminocarbonyl]-2-(1H-indol-3-yl)-ethyl]-carbamate as an orange oil which was used as is in the following step.

STEP C: 1,1-dimethylethyl N-[(S) 1-[4-hydroxy-3-[(2-thiazolylamino)-carbonyl]-8-(trifluoromethyl)-quinolin-2-yl]-2-(1H-indol-3-yl)-ethyl]-carbamate Using the procedure of Step C of Example 7, a solution of 28 g of the product of Step B in 280 ml of tetrahydrofuran and 5.25 g of dimethylaminopyridine were reacted to obtain 16.9 g of 1,1-dimethylethyl N-[(S) 1-[4-hydroxy-3-[(2-thiazolylamino)-carbonyl]-8-(trifluoromethyl)-quinolin-2-yl]-2-(1H-indol-3-yl)-ethyl]-carbamate melting at 270° C. and having a specific rotation of [α]$_D$= +33°±2° (c=0.5% in CH$_3$COOH).

Analysis: Calculated: %C, 58.28; %H, 4.38; %N, 11.72; %F, 9.54; %S, 5.36. Found: %C, 58.3; %H, 4.4; %N, 11.4; %F, 9.3; %S, 5.4.

EXAMPLE 12

2-[(S) 1-amino-2-(1H-indol-3-yl)-ethyl]-4-hydroxy-N-(2-thiazolyl)-8-trifluoromethyl-3-quinoline carboxamide A mixture of 16.9 g of product of Example 11, 170 ml of methylene chloride and 85 ml of trifluoroacetic acid was stirred for 3 hours at ambient temperature and the solvents were eliminated under reduced pressure. The crude oil residue was crystallized from ether and after filtering, rinsing and drying under reduced pressure at 50° C., 16.4 g of 2-[(S) 1-amino-2-(1H-indol-3-yl)-ethyl]-4-hydroxy-N-(2-thiazolyl)-8-trifluoromethyl-3-quinoline carboxamide were obtained in the form of trifluoroacetate melting at about 190° C.

The said 16.4 g of product were introduced into 200 ml of water and the solution was extracted with 200 ml of ethyl acetate. The organic phase was washed with water, dried and concentrated to dryness under reduced pressure. The residue was crystallized from ether, then separated and dried under reduced pressure. The residue was dissolved in 100 ml of acetonitrile at ambient temperature and the crystals were frozen, filtered and dried under reduced pressure at 90° C. to obtain 7.830 g of crude product which was crystallized from isopropanol. After having expelled the isopropanol under reduced pressure, the residue was triturated in acetonitrile. After filtering and drying under reduced pressure, the residue was taken up in 20 ml of ethyl acetate, filtered and dried under reduced pressure at 100° C. to obtain 4.8 g of 2-[(S) 1-amino-2-(1H-indol-3-yl)-ethyl]-4-hydroxy-N-(2-thiazolyl)-8-trifluoromethyl-3-quinoline carboxamide melting at 190° C. and having a specific rotation of [α]$_D$= +47°±1° (c=1% DMF).

Analysis: Calculated: %C, 57.94; %H, 3.65; %N, 14.08; %F, 11.46; %S, 6.44. Found: %C, 57.7; %H, 3.9; %N, 13.0; %F, 10.6; %S, 6.2.

EXAMPLE 13

1,1-dimethylethyl N-[(S) 1-[4-hydroxy-3-(2-thiazolylaminocarbonyl)-8-trifluoromethyl)-quinolin-2-yl]-2-(phenyl)-ethyl]-carbamate STEP A: 1,1-dimethylethyl N-[(S) 2-phenyl-1-[4-oxo-8-(trifluoromethyl)-4H-3,1-benzoxazin-2-yl]-ethyl]-carbamate Using the procedure of Step A of Example 7, a solution of 19.9 g of BOC-L-phenylalanine in 150 ml of methylene chloride and 20.6 ml of N-methyl-morpholine, 19.5 ml of isobutyl chloroformate in 75 ml of methylene chloride and 15.4 g of 2-amino-3-trifluoromethyl benzoic acid in 150 ml of methylene chloride and 8.3 ml of N-methyl-morpholine were reacted to obtain 14.5 g of 1,1-dimethylethyl N-[(S) 2-phenyl-1-[4-oxo-8-(trifluoromethyl)-4H-3,1-benzoxazin-2-yl]-ethyl]-carbamate melting at 145° C. and having a specific rotation of [α]$_D$= −33.5°±2° (c=0.5% in CH$_3$COOH).

Analysis: Calculated: %C, 60.83; %H, 4.87; %N, 6.45; %F, 13.12. Found: %C, 60.6; %H, 4.9; %N, 6.5; %F, 12.8.

STEP B: 1,1-dimethylethyl N-[(S) 1-[[2-[1,3-dioxo-3-(2-thiazolylamino)-propyl]-6-(trifluoromethyl)-phenyl]-amino-carbonyl]-2-(phenyl)-ethyl]-carbamate Using the procedure of Step B of Example 7, a solution of 9.09 g of 2-acetylaminothiazole in 280 ml of tetrahydrofuran, 91 ml of n-butyllithium in solution in hexane and 13.9 g of product of Step A in 100 ml of tetrahydrofuran were reacted to obtain 19 g of 1,1-dimethylethyl N-[(S) 1-[[2-[1,3-dioxo-3-(2-thiazolylamino)-propyl]-6-(trifluoromethyl)-phenyl]-amino-carbonyl]-2-(phenyl)-ethyl]-carbamate.

STEP C: 1,1-dimethylethyl N-[(S) 1-[4-hydroxy-3-[(2-thiazolylaminocarbonyl)-8-(trifluoromethyl)-quinolin-2-yl]-2-(phenyl)-ethyl]-carbamate Using the procedure of Step C of Example 7, a solution of 18.7 g of the product of Step B, 190 ml of tetrahydrofuran and 3.9 g of 4-dimethylaminopyridine were reacted to obtain 17.4 g of 1,1-dimethylethyl N-[(S) 1-[4-hydroxy-3-[(2-thiazolyl-aminocarbonyl)-8-(trifluoromethyl)-quinolin-2-yl]-2-(phenyl)-ethyl]-carbamate melting at 268° C. and having a specific rotation of [α]$_D$= +44°±3° (c=0.25% DMF)

Analysis: Calculated: %C, 58.06; %H, 4.51; %N, 10.03; %F, 10.2; %S, 5.74. Found: %C, 58.0; %H, 4.5; %N, 9.9; %F, 10.4; %S, 6.0.

EXAMPLE 14

2-[(S) 1-amino-2-phenylethyl]-4-hydroxy-N-(2-thiazolyl)-8-trifluoromethyl)-3-quinoline carboxamide A mixture of 16.9 g of the product of Example 13, 300 ml of methylene chloride and 85 ml of trifluoroacetic acid was stirred for 2 hours at ambient temperature and then the solvents were eliminated under reduced pressure. An oil which crystallized spontaneously from ether was obtained and after filtering, washing, drying under reduced pressure, 11.9 g of 2-[(S) 1-amino-2-phenylethyl]-4-hydroxy-N-(2-thiazolyl)-8-trifluoromethyl)-3-quinoline carboxamide in the form of trifluoroacetate melting at 190° C. were obtained.

The said product was introduced into 100 ml of water with stirring and a saturated aqueous solution of sodium bicarbonate was added until a pH of 8 was reached. The mixture was stirred for 30 minutes at ambient temperature and after filtering, the product was washed with water several times until a pH of 2-3 was reached and dried under reduced pressure to obtain 9.3 g of crude product which was dissolved in 80 ml of dimethylformamide and filtered. 160 ml of ether were added to the filtrate and after cooling, the crystals obtained were separated, washed with ether and dried under reduced pressure at ambient temperature to obtain 2.5 g of 2-[(S) 1-amino-2-phenylethyl]-4-hydroxy-N-(2-thiazolyl)-8-trifluoromethyl)-3-quinoline carboxamide melting at 248°-250° C. (1st crystalline form). A second lot was obtained from the previous dimethylformamide ether filtrate by evaporations. The solvents were removed under reduced pressure to obtain an orange oil which crystallized from ether. After filtering, washing, drying under reduced pressure, dissolving the residue in tetrahydrofuran, filtering, concentrating the filtrate and adding ether, cooling, separating and drying the product, 4.52 g of 2-[(S) 1-amino-2-phenylethyl]-4-hydroxy-N-(2-thiazolyl)-8-(trifluoromethyl)-3-quinoline carboxamide melting at 234° C. (2nd crystalline form) were obtained.

EXAMPLE 15

1,1-dimethylethyl (2S)-2-[4-hydroxy-3-[(2-thiazolylamino)-carbonyl]-8-(trifluoromethyl)-quinolin-2-yl]-1-pyrrolidine carboxylate STEP A: 1,1-dimethylethyl (2S) 2-[4-oxo-8-(trifluoromethyl)-4H-3,1-benzoxazin-2-yl]-1-pyrrolidine carboxylate Using the procedure of Step A of Example 7, a solution of 16.14 ml of BOC-L-proline in 150 ml of methylene chloride, 20.6 ml of N-methyl-morpholine, 19.5 ml of isobutyl chloroformate in 75 ml of methylene chloride and 15.4 g of 2-amino-3-trifluoromethylbenzoic acid in 150 ml of methylene chloride and 8.3 ml of N-methyl-morpholine were reacted for 20 hours. The mixture was extracted with methylene chloride and the residue was chromatographed on silica gel and was eluted with methylene chloride to obtain 16.4 g of 1,1-dimethylethyl (2S) 2-[4-oxo-8-(trifluoromethyl)-4H-3,1-benzoxazin-2-yl]-1-pyrrolidine carboxylate having a specific rotation of $[\alpha]_D = -75° \pm 2.5°$ (c=0.6% in CH$_3$COOH).

STEP B: 1,1-dimethylethyl (2S) 2-[[2-[1,3-dioxo-3-(2-thiazolylamino)-propyl]-6-trifluoromethyl-phenyl]-aminocarbonyl]-1-pyrrolidine carboxylate Using the procedure of Step B of Example 1, a solution of 11.8 g of N-2-thiazolyl-acetamide in 360 ml of tetrahydrofuran, 119 ml of a solution of N-butyllithium in hexane and 16 g of the product of Step A in 100 ml of tetrahydrofuran were reacted to obtain 9.0 g of 1,1-dimethylethyl (2) 2-[[2-[1,3-dioxo-3-(2-thiazolylamino)-propyl]-6-trifluoromethyl-phenyl]-aminocarbonyl]-1-pyrrolidine carboxylate melting at 136°-138° C. and having a specific rotation of $[\alpha]_D = -49° \pm 1°$ (c=1% in CH$_3$COOH).

Analysis: C$_{23}$H$_{25}$N$_4$F$_3$O$_5$S: Molecular weight=526.543. Calculated: %C, 52.47; %H, 4.78; %N, 10.64; %F, 10.83; %S, 6.09. Found: %C, 52.8; %H, 4.9; %N, 10.3; %F, 10.7; %S, 6.0.

STEP C: 1,1-dimethylethyl (2S) 2-[4-hydroxy-3-[(2-thiazolylamino)-carbonyl]-8-(trifluoromethyl)-quinolin-2-yl]-1-pyrrolidine carboxylate A mixture of 11.1 g of the product of Step B, 110 ml of tetrahydrofuran and 2.6 g of 4-dimethyl-aminopyridine was stirred for 24 hours at ambient temperature and after heating to reflux, the tetrahydrofuran was eliminated under reduced pressure. The residue was taken up in 100 ml of water and 10.5 ml of 2N hydrochloric acid. The precipitate was dissolved in ethyl acetate and the organic solution was washed with water, dried and concentrated to dryness under reduced pressure. The product was crystallized from ether to obtain 9.1 g of 1,1-dimethylethyl (2S) 2-[4-hydroxy-3-[(2-thiazolylamino)-carbonyl]-8-(trifluoromethyl)-quinolin-2-yl]-1-pyrrolidine carboxylate melting at 215° C. and having a specific rotation of $[\alpha]_D = -55° \pm 1.5°$ (c=1% in CH$_3$COOH).

Analysis: C$_{23}$H$_{23}$N$_4$O$_4$F$_3$S: molecular weight=508.538. Calculated: %C, 54.32; %H, 4.56; %N, 11.02; %F, 11.21; %S, 6.30. Found: %C, 54.5; %H, 4.7; %N, 10.8; %F, 11.1; %S, 6.2.

EXAMPLE 16

4-hydroxy-2-[(2S) 2-pyrrolidinyl]-N-(2-thiazolyl)-8-trifluoromethyl-3-quinoline carboxamide Using the procedure of Example 14, 7.8 g of the product of Example 11, 80 ml of methylene chloride, and 40 ml of trifluoroacetic acid were reacted to obtain 8.0 g of 4-hydroxy-2-[(2S) 2-pyrrolidinyl]-N-(2-thiazolyl)-8-trifluoromethyl-3-quinoline carboxamide in the form of its trifluoroacetate melting at 210° C.

8 g of the trifluoroacetate were introduced in 100 ml of water and the mixture was extracted with ethyl acetate. The organic phase was washed with water to a pH of 4, dried and concentrated to dryness under reduced pressure. The residue was taken up in 80 ml of acetonitrile and the crystals obtained were separated and dried at 80° C. under reduced pressure to obtain 4.7 g of 4-hydroxy-2-[(2S) 2-pyrrolidinyl]-N-(2-thiazolyl)-8-trifluoromethyl-3-quinoline carboxamide melting at 196° C. and having a specific rotation of $[\alpha]_D = -7° \pm 1°$ (c=1% in CH$_3$COOH).

Analysis: C$_{18}$H$_{15}$F$_3$N$_4$O$_2$S: molecular weight=408.411. Calculated: %C, 52.94; %H, 3.70; %N, 13.72; %F, 13.96; %S, 7.85. Found: %C, 52.4; %H, 3.6; %N, 13.4; %F, 13.9; %S, 7.8.

EXAMPLE 17

1,1-dimethylethyl N-[1-[4-hydroxy-3-[(2-thiazolylamino)-carbonyl]-8-(trifluoromethyl)-quinolin-2-yl]-2-(phenylmethoxy)-ethyl]-carbamate STEP A: 1,1-dimethylethyl N-[1-[4-oxo-8-trifluoromethyl-4H-3,1-benzoxazin-2-yl]-2-(phenylmethoxy)-ethyl]-carbamate Using the procedure of Step A of Example 7, a solution of 29.5 g of BOC-O-benzyl L-serine in 200 ml of methylene chloride, 27.5 ml of N-methyl-morpholine, 26.2 g of isobutyl chloroformate in methylene chloride and 20.5 g of 2-amino-3-trifluoromethyl benzoic acid in 200 ml of methylene chloride and 11 ml of N-methyl-morpholine were reacted for 16 hours. The mixture was extracted with methylene chloride and chromatography on silica gel (eluent: methylene chloride) yielded 18.5 g of 1,1-dimethylethyl N-[1-[4-oxo-8-trifluoromethyl-4H-3,1-benzoxazin-2-yl]-2-(phenylmethoxy)-ethyl]-carbamate melting at 98° C.

Analysis: $C_{23}H_{23}N_2O_5F_3$: molecular weight=464.449. Calculated: %C, 59.48; %H, 4.49; %N, 6.03; %F, 12.27. Found: %C, 59.2; %H, 5.0; %N, 6.0; %F, 12.3.

STEP B: 1,1-dimethylethyl N-[2-[[2-[1,3-dioxo-3-[(2-thiazolyl)-amino]-propyl]-6-trifluoromethylphenyl]-amino]-2-oxo-1-[(phenylmethoxy)-methyl]-ethyl]-carbamate Using the procedure of Step B of Example 1, a solution of 11.14 g of N-2-thiazolyl acetamide in 350 ml of tetrahydrofuran, 112 ml of N-butyllithium in hexane and 18.2 g of product of Step A in 100 ml of tetrahydrofuran were reacted to obtain 15.8 g of 1,1-dimethylethyl N-[2-[[2-[1,3-dioxo-3-[(2-thiazolyl)-amino-propyl]-6-trifluoromethylphenyl]-amino]-2-oxo-1-[(phenyl-methoxy)-methyl]-ethyl]-carbamate melting at 134°-136° C.

Analysis: $C_{22}H_{29}N_4O_6F_3S$: molecular weight=606.63. Calculated: %C, 55.44; %H, 4.82; %N, 9.24; %F, 9.40; %S, 5.28. Found: %C, 55.7; %H,4.7; %N, 9.3; %F, 9.4; %S, 5.4.

STEP C: 1,1-dimethylethyl N-[1-[4-hydroxy-3-[(2-thiazolylamino)-carbonyl]-8-(trifluoromethyl)-quinolin-2-yl]-2-(phenylmethoxy)-ethyl]-carbamate A mixture of 15.5 g of the product of Step B in 150 ml of tetrahydrofuran and 3.1 g of 4-dimethylaminopyridine was stirred for 6 hours at ambient temperature and the solution was poured into 400 ml of water with 20 ml of 2N hydrochloric acid added. The mixture was extracted with a mixture of ethyl acetate and tetrahydrofuran and the organic phase was washed with water, dried, concentrated to dryness under reduced pressure. The residue was crystallized from ether and dried at 70° C. at reduced pressure to obtain 13.6 g of 1,1-dimethylethyl N-[1-[4-hydroxy-3-[(2-thiazolylamino)-carbonyl]-8-(trifluoromethyl)-quinolin-2-yl]-2-(phenylmethoxy)-ethyl]-carbamate melting at 208° C.

Analysis: $C_{28}H_{27}O_5N_4F_3S$: molecular weight=588.615. Calculated: %C, 57.14; %H, 4.62; %N, 9.52; %F, 9.68; %S, 5.44. Found: %C, 57.1; %H, 4.5; %N, 9.5; %F, 9.9; %S, 5.5.

EXAMPLE 18

2-(1-amino-2-hydroxyethyl)-4-hydroxy-N-(2-thiazolyl)-8-trifluoromethyl)-3-quinoline carboxamide A solution of 10.3 g of the product of Example 17 in 300 ml of methylene chloride was cooled to −20° and 131.25 ml of a molar solution of boron tribromide in methylene chloride were added. Stirring was maintained for 1 hour at −20° C. and then for 2 hours at ambient temperature. The mixture was poured into 800 ml of water and was extracted with methylene chloride, ethyl acetate and tetrahydrofuran. The organic phase was washed with water, dried and concentrated to dryness under reduced pressure. The residue was crystallized from ether to obtain in two lots. 4.98 g of crude product were dissolved in 180 ml of tetrahydrofuran and 50 ml of water. After adding active carbon and filtering over silica, the filtrate was concentrated under reduced pressure until crystals appear. After cooling, separating the crystallized product and washing with tetrahydrofuran and drying at 80° C. under reduced pressure, 2.7 g of 2-(1-amino-2-hydroxyethyl)-4-hydroxy-N-(2-thiazolyl)-8-trifluoromethyl)-3-quinoline carboxamide melting at 248° C. were obtained.

Analysis: $C_{16}H_{13}O_3N_4F_3S$: molecular weight=398.371. Calculated: %C, 48.24; %H, 3.29; %N, 14.06; %F, 14.31; %S, 8.05. Found: %C, 47.9; %H, 3.3; %N, 13.6; %F, 14.4; %S, 8.0.

EXAMPLE 19

2-[(1S) 1-(acetylamino)-propyl]-4-hydroxy-N-(2-thiazolyl)-8-trifluoromethyl-3-quinoline carboxamide 10 ml of acetic anhydride and 6 g of 2-[(1S) 1-aminopropyl]-4-hydroxy-N-(2-thiazolyl)-8-trifluoromethyl-3-quinoline carboxamide of Example 8 were added dropwise with stirring to 60 ml of pyridine and stirring was maintained for 90 minutes at ambient temperature. The solution was poured into 150 ml of iced water and concentrated hydrochloric acid was added until a pH of 1. The precipitate was filtered, washed with water and then dissolved in tetrahydrofuran. The organic phase was dried, and concentrated to dryness under reduced pressure. The residue was taken up in ether, filtered and dried under reduced pressure at 80° to obtain 5.3 g of 2-[(1S) 1-(acetylamino)-propyl]-4-hydroxy-N-(2-thiazolyl)-8-trifluoromethyl-3-quinoline carboxamide melting at 275° C. and having a specific rotation of $[\alpha]_D = +43.5°\pm 4°$ (c=0.3% in DMF).

Analysis: $C_{19}H_{17}O_3N_4F_3S$: molecular weight=438.436. Calculated: %C, 52.05; %H, 3.91; %N, 12.78; %F, 13.00; %S, 7.31. Found: %C, 51.8; %H, 3.8; %N, 12.4; %F, 13.1; %S, 7.2.

EXAMPLE 20

4-hydroxy-2-[(S) 1-[(1-oxopropyl)-amino]-propyl]-N-(2-thiazolyl)-8-trifluoromethyl-3-quinoline carboxamide Using the procedure of Example 19, 3.2 g of 2-[(S) 1-[aminopropyl]-4-hydroxy-N-(2-thiazolyl)-8-trifluoromethyl]-3-quinoline carboxamide of Example 8, 32 ml of pyridine and 6.6 ml of propionic anhydride were reacted to obtain 3.0 g of 4-hydroxy-2-[(S) 1-[(1-oxopropyl)-amino]-propyl]-N-(2-thiazolyl)-8-trifluoromethyl-3-quinoline carboxamide melting at >275° and having a specific rotation of $[\alpha]_D = +57.5°\pm 2.5°$ (c=0.5% in CH₃COOH).

Analysis: $C_{20}H_{19}F_3N_4O_3S$: molecular weight=452.458. Calculated: %C, 53.09; %H, 4.23; %N, 12.38; %F, 12.60; %S, 7.09. Found: %C, 53.0; %H, 4.3; %N, 12.1; %F, 12.8; %S, 7.1.

EXAMPLE 21

1,1-dimethylethyl N-(S)-[2-[4-hydroxy-3-[(2-thiazolylamino)-carbonyl]-8-trifluoromethyl-quinolin-2-yl]-[2-methylpropyl]-amino]-2-oxoethyl]-carbamate A solution of 4.38 g of N-BOC Glycine, 40 ml of methylene chloride and 2.75 ml of N-methyl-morpholine was cooled to −25° C. and 3.41 ml of isobutyl chloroformate in solution in 30 ml of methylene chloride were added. After stirring for 25 minutes at −25° C., a solution of 8.56 g of 2-[(S) 1-amino-2-methyl-propyl]-4-hydroxy-N-(2-thiazolyl)-8-trifluoromethyl-3-quinoline carboxamide from Example 12 starting with trifluoroacetate of Example 8 in 80 ml of tetrahydrofuran was added. Stirring was maintained for 1 hour at −25° C. and the reaction mixture was poured into 300 ml of water. 2N hydrochloric acid was added until the pH was 1. After extraction with methylene chloride, the organic phase was washed with water, then with a saturated aqueous solution of sodium bicarbonate, then water, dried and concentrated to dryness under reduced pressure. The oily residue was taken up in petroleum ether (b.p.=60°−80°) and the crystals obtained were separated and dried at 60° C. under reduced pressure to obtain 11.15 g of 1,1-dimethylethyl N-(S)-[2-[4-hydroxy-3-[(2-thiazolylamino)-carbonyl]-8-trifluoromethyl-quinolin-2-yl]-[2-methylpropyl]-amino]-2-oxoethyl]-carbamate melting at ≃170° C. and having a specific rotation of $[\alpha]_D = +37°\pm 2°$ (c=0.5% in $CH_3COOH$).

EXAMPLE 22

2-[(1S) 1-[(aminoacetyl)-amino]-2-methylpropyl]-4-hydroxy-N-(2-thiazolyl)-8-trifluoromethyl-3-quinoline carboxamide (monohydrate)

A solution of 9.6 g of the product of Example 21 in 50 ml of methylene chloride was stirred while 20 ml of an ethanol solution of 5.7N hydrochloric acid were added dropwise. The mixture was stirred for 16 hours at ambient temperature and 10 ml more of ethanol solution were added. The mixture was stirred for 1 hour and the solvents were eliminated under reduced pressure at a temperature lower than 40° C. The residue was dissolved in water, active carbon was added and the solution was filtered on silica. The pH was adjusted to 8 with a saturated aqueous solution of sodium bicarbonate, then, after separating, washing with water and drying under reduced pressure at 70° C., 6.7 g of crude product were obtained. 4.48 g of this product were dissolved in 20 ml of dimethylformamide at ambient temperature and then was filtered on silica. 25 ml of water was added and after cooling and separating, the crystallized product was dried under reduced pressure at 50° C. for 16 hours to obtain 3.6 g of 2-[(1S) 1-[(aminoacetyl)-amino]-2-methylpropyl]-4-hydroxy-N-(2-thiazolyl)-8-trifluoromethyl-3-quinoline carboxamide (monohydrate) melting at 230° C. and having a specific rotation of $[\alpha]_D = +72\pm 1.5°$ (c=1% in $CH_3COOH$).

Analysis: $C_{20}H_{20}N_5O_3F_3S,H_2O$: molecular weight=485.50. Calculated: %C, 49.47; %H, 4.56; %N, 14.42; %F, 11.74; %S, 6.60. Found: %C, 49.1; %H, 4.7; %N, 14.3; %F, 11.3; %S, 6.4.

EXAMPLE 23

Tablets were prepared containing 50 mg of the product of Example 6 or 30 mg of the product of Example 8 and sufficient excipient of lactose, talc, starch and magnesium stearate for a final tablet weight of 350 mg.

PHARMACOLOGICAL STUDY OF PRODUCTS OF EXAMPLES 6 AND 8

A. Analgesic Activity

The test was based on the fact noted by KOSTER et al [Fed. Proc. (1959) Vol. 1B page 412] by which the interperitoneal injection of acetic acid provoked in mice repeated movements of stretching and twisting which persisted for more than 6 hours. Analgesics prevent or diminish this syndrome which can be considered as the expression of a diffuse abdominal pain. A solution of 1% acetic acid in water was used and the dose causing the syndrome was under these conditions from 0.01 $cm^3/g$, or 100 mg/kg of acetic acid. The test product was administered by intra-veinous route half an hour before the injection of acetic acid, the mice having fasted since the day before the experiment. The stretchings were observed and counted for each mouse for an observation period of 15 minutes beginning immediately after the acetic acid injection. The results, expressed as $DA_{50}$, that is to say the dose which effected a reduction of 50% of the number of stretchings in comparison with the control animals, were found to be 2 mg/kg and 7 mg/kg, respectively, for the products of Examples 6 and 8.

B. Anti-inflammatory Activity: Chronic Arthritis of Adjuvant

The injection of "Freund" type adjuvant into a hind leg provoked in rats the rapid appearance of a primary inflammatory lesion in this leg, then after a latent period of 13 to 15 days, the causing of a secondary arthritis, effecting in particular the other hind leg. The test was effected on male rates aged from 42 to 50 days which received an intraplantar injection of 0.1 ml of adjuvant of "Freund" type (suspension in vaseline oil of 6 mg per ml of killed mycobacterium butyricum). The animals received the test product orally, from day 0 (day of the injection of the adjuvant) until the day before they were killed which occured on day 17. The control arthritic animals and normal control animals only received the vehicle. The assessment criteria of the activity of the substances studied were the increase in the volume of hind legs injected (primary and secondary inflammation) and not injected (secondary inflammation) in comparison with the average volume of legs corresponding to the normal controls.

The $DA_{50}$, that is the dose which reduced the increase in volume of the hind legs of the animals treated in comparison to the control animals by 50% was determined to be 5 mg/kg and 3 mg/kg, respectively, for the products of Examples 6 and 8.

Various modifications of the products and methods of the invention may be made without departing from the spirit or scope thereof and it is to be understood that the invention is intended to be limited only as defined in the appended claims.

What we claim is:

1. A compound selected from the group consisting of racemates or optically active forms of the formula

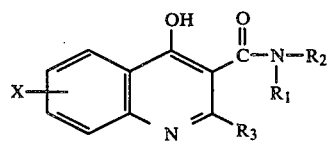

I wherein X is in the 5-, 6-, 7- or 8-position and is selected from the group consisting of hydrogen, halogen, alkyl of 1 to 5 carbon atoms, alkoxy of 1 to 4 carbon atoms, $CF_3-$, $CF_3S-$ and $CF_3O-$, $R_1$ is selected from the group consisting of hydrogen and alkyl of 1 to 4 carbon atoms, $R_2$ is selected from the group consisting of (a)

thiazolyl, 4,5-dihydrothiazolyl, pyridinyl, oxazolyl, isoxazolyl, imidazolyl, pyrimidyl and tetrazolyl, each optionally substituted with alkyl of 1 to 4 carbon atoms and (b) phenyl optionally substituted with at least one member of the group consisting of hydroxy, alkyl and alkoxy of 1 to 4 carbon atoms, $CF_3—$, $—NO_2$ and halogen, $R_3$ is selected from the group consisting of 2-pyrrolidinyl of the formula

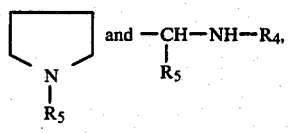

$R_4$ is selected from the group consisting of hydrogen, $—COOA$ and A is selected from the group consisting of alkyl of 1 to 5 carbon atoms, aryl of 6 to 10 carbon atoms and aralkyl of 7 to 12 carbon atoms and

$R_4'$ is selected from the group consisting of alkyl of 1 to 5 carbon atoms optionally substituted with amino or protected amino, aryl of 6 to 10 carbon atoms and aralkyl of 7 to 12 carbon atoms, $R_5$ is selected from the group consisting of hydrogen, alkyl of 1 to 5 carbon atoms, aryl of 6 to 10 carbon atoms, aralkyl of 7 to 12 carbon atoms, p-hydroxy-benzyl, 1H-indol-3-yl methyl of the formula

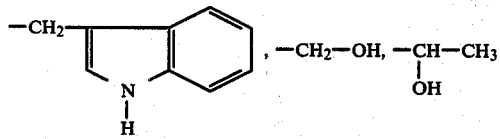

and $—CH_2SH$, the last three being optionally protected by a blocking group and their non-toxic, pharmaceutically acceptable acid addition salts.

2. A compound of claim 1 wherein X is 8-$CF_3$.

3. A compound of claim 1 wherein $R_1$ is hydrogen and $R_2$ is thiazolyl.

4. A compound of claim 1 wherein A is benzyl or tert.-butyl.

5. A compound of claim 1 wherein $R_4$ is hydrogen.

6. A compound of claim 1 in its optically active (S) form.

7. An analgesic and anti-inflammatory composition comprising an analgesically and anti-inflammatorily effective amount of at least one compound of claim 1 and a pharmaceutical carrier.

8. A composition of claim 7 wherein in the compound X is 8-$CF_3$.

9. A composition of claim 7 wherein in the compound $R_1$ is hydrogen and $R_2$ is thiazolyl.

10. A composition of claim 7 wherein in the compound the amino protective group has the formula $—COOA$ and A is selected from the group consisting of alkyl of 1 to 5 carbon atoms, aryl of 6 to 10 carbon atoms and aralkyl of 7 to 12 carbon atoms.

11. A composition of claim 7 wherein in the compound A is benzyl or tert.-butyl.

12. A composition of claim 7 wherein the compound is in its optically active (S) form.

13. A method of relieving pain and inflammation in warm-blooded animals comprising administering to warm-blooded animals an analgesically and anti-inflammatorily effective amount of at least one compound of claim 1.

14. A method of claim 13 wherein the compound X is 8-$CF_3$.

15. A method of claim 13 wherein in the compound $R_1$ is hydrogen and $R_2$ is thiazolyl.

16. A method of claim 13 wherein in the compound A is benzyl or tert.-butyl.

17. A method of claim 13 wherein in the compound $R_4$ is hydrogen.

18. A method of claim 13 wherein the compound is in its optically active (S) form.

* * * * *